United States Patent [19]

Tanie et al.

[11] 4,254,776

[45] Mar. 10, 1981

[54] APPARATUS FOR TRANSMISSION OF INFORMATION BY ELECTROCUTANEOUS STIMULI

[75] Inventors: Kazuo Tanie, Yokohama; Susumu Tachi, Tokyo, both of Japan

[73] Assignees: Agency of Industrial Science & Technology, Japan; Ministry of International Trade & Industry, both of Tokyo, Japan

[21] Appl. No.: 7,425

[22] Filed: Jan. 29, 1979

Related U.S. Application Data

[63] Continuation-in-part of Ser. No. 864,711, Dec. 27, 1977, abandoned.

[30] Foreign Application Priority Data

Dec. 28, 1976 [JP] Japan .................................. 51-159080

[51] Int. Cl.$^3$ ............................................. A61N 1/36
[52] U.S. Cl. ..................................... 128/421; 128/908
[58] Field of Search ............ 128/419 PG, 421 R, 422, 128/423 R, 783, 908

[56] References Cited

U.S. PATENT DOCUMENTS

| 2,703,344 | 3/1955 | Anderson | 128/783 |
| 3,554,198 | 1/1971 | Tatolan et al. | 128/908 |
| 3,851,651 | 12/1974 | Icenbice, Jr. | 128/422 |
| 3,910,257 | 10/1975 | Fletcher et al. | 128/908 |

Primary Examiner—William E. Kamm
Attorney, Agent, or Firm—Kurt Kelman

[57] ABSTRACT

An apparatus for use in a system for transmitting information in the form of electric stimuli to a subject through the medium of a multiplicity of electrodes attached to the subject, which apparatus comprises analogue switches provided one each for the electrodes at their respective input sides and a decoder adapted to effect the "ON-OFF" control of these analogue switches. The pulse signals generated by a stimulator to represent a given piece of information are transmitted to the analogue switches, and then the pulse signals are applied to the subject only through the electrodes which are in their "ON" state at the time of the reception of the signals, giving required electric stimuli to the subject.

4 Claims, 9 Drawing Figures

APPARATUS FOR TRANSMISSION OF INFORMATION BY ELECTROCUTANEOUS STIMULI

REFERENCE TO COPENDING APPLICATION

This is a continuation-in-part application of our copending application U.S. Ser. No. 864,711 filed Dec. 27, 1977, now abandoned.

BACKGROUND OF THE INVENTION

This invention relates to an apparatus for the transmission of information to a subject through application of electric stimuli, which apparatus effects transmission of information by causing a stimulator to generate pulse signals in conformity with the information and allowing the pulse signals to be conveyed to the skin of the subject only through the selected ones of an array of electrodes attached to the skin.

Efforts are being made to utilize the system of transmission of information by the medium of electrocutaneous stimuli to the human organism as a means of facilitating the operation of prosthetic arms or manipulators by the user by enabling the sensation of touch or sensation of force to be fed back to the user or as a means of providing deaf and/or blind persons with substitutive audio and/or visual sensation, respectively.

Generally in the transmission of information by the electrocutaneous stimuli, a relevant collection of signals is issued in the form of a train of pulses which carries the information in terms of the frequency of repetition of certain pulses, the height of pulses, the width of pulses or the duration of the train of pulses. In the transmission of information by the method described above, if a set of signals desired to be transmitted is converted into a train of pulses and delivered in that form to the skin of the human subject, the magnitude of sensation caused in the skin by the same pulse signals may vary from time to time because of variations in the subject's cutaneous impedance. For this reason, there are times at which the method fails to provide correct transmission of information. The present inventors conducted a study in search of a solution to this problem. They, consequently, ascertained that pulse signals differing in pulse height or pulse width, in the case of information transmission by electrocutaneous stimulation on the human skin, generate thereon one and the same magnitude of sensation when the products of pulse widths multiplied by the squares of respective pulse heights are equal. Based on this knowledge, they suggested a method for correct transmission of information (U.S. patent application Ser. No. 781,887) which comprises preparatorily measuring the cutaneous impedance of a given subject and, on the basis of the results of this measurement, making a necessary correction in the pulse height or pulse width of the pulse signal so as to represent the information to be transmitted, while eliminating the effect of the cutaneous impedance change of that particular subject and ensuring correct transmission of the information.

Since different pulse signals generate the same magnitude of sensation on the human organism when the products of pulse widths multiplied by the squares of respective pulse heights are equal, the only physical parameters that are available for electrocutaneous communication are frequency, energy and duration time of the electric pulse. However, if these parameters alone in electrocutaneous communication are used, maximum capacity of information to be transmitted is from 3 to 5 bits in each case. For a larger amount of complicated information to be successfully transmitted, therefore, it becomes necessary to expand the region of the organism subjected to electrocutaneous stimuli, i.e. to set a multiplicity of electrodes on the subject's skin.

When electric signals are conveyed to the skin through a multiplicity of electrodes attached to the skin, it is necessary that each of the electric routes should be provided with an electric stimulator and an isolator (as disclosed in U.S. Pat. Nos. 3,848,608 and 3,646,940, for example). To ensure independence of the individual electrodes, it is necessary that each of the electrodes should be provided with an isolator.

Where complicated information is to be transmitted by use of a multiplicity of electrodes as described above, the operation is not only uneconomical because of the inevitable use of a multiplicity of expensive parts but also quite hazardous because of the possible simultaneous application of electric signals through the multiplicity of electrodes and the consequent instantaneous transmission of a large electric energy to the human organism.

An object of the present invention is to provide an apparatus for use in the system which transmits information in the form of electric stimuli to the subject through the medium of a multiplicity of electrodes attached to the subject, which apparatus is simple in construction and is capable of accurately conveying information of high complexity.

Another object of the present invention is to provide an apparatus for the transmission of information in the form of electric stimuli to the subject, which apparatus enables complicated information to be conveyed to the subject accurately without jeopardizing the safety of the subject.

SUMMARY OF THE INVENTION

To accomplish the objects described above according to the present invention, there is provided an apparatus for use in the system which is composed of a central processing unit, an input unit for feeding to the CPU the information subjected to transmission, a stimulator for generating trains of pulse signals in accordance with the commands issuing from the CPU, a plurality of electrodes attached to the subject and adapted to impart electric stimuli to the subject upon reception of the pulse signals from the stimulator, and an isolator for electrically isolating the human subject from the stimulator, which apparatus comprises analogue switches provided one each for the plurality of electrodes attached to the human subject at the input sides thereof, a decoder adapted to effect the "ON-OFF" control of the analogue switches and an isolator serving as a medium through which the analogue switches are connected with the decoder.

When the CPU issues a command in conformity with the information subjected to transmission and the stimulator generates a train of pulse signals in accordance with the command from the CPU and transmits it toward the electrodes, the pulse signals are conveyed to the analogue switches of the electrodes. Then, they are forwarded only through those electrodes whose analogue switches happen to be in their "ON" state at the time of the reception of pulse signals. The electric stimuli are imparted to the subject only through these electrodes. When a train of pulse signals is applied to a human being with not more than 15 ms elapsing between the first and final pulses of the train, the human being perceives that all the pulse signals have been applied all at once. When a series of pulse signals is generated by the stimulator and, at the same time, the "ON-OFF" signals for the analogue switches are issued by the decoder and conveyed to the relevant analogue switches, the subject receives electric stimuli which have the same effect as those received when pulse signals from a multiplicity of stimulators are simultaneously applied to the subject through the relevant electrodes. Thus, the apparatus of the present invention enjoys economy due to the simplicity of construction and precludes the otherwise possible dangers to the human subject owing to the simultaneous application of multiplicity of pulse signals.

The other objects and characteristic features of the present invention will become apparent from a description to be given specifically hereinafter with reference to the accompanying drawing.

DESCRIPTION OF THE PREFERRED EMBODIMENTS

Figure 1:
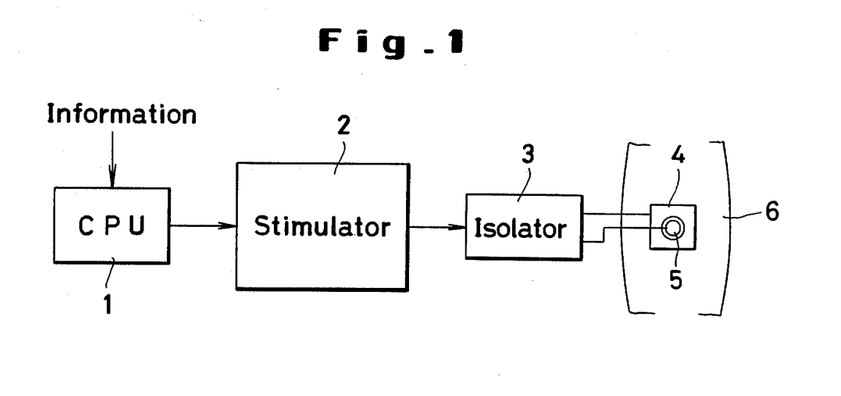
FIG. 1 is a block diagram of an apparatus for the transmission of information by the medium of electrocutaneous stimuli.

The principle for the transmission of information by means of electrocutaneous stimuli will be described with reference to FIG. 1.

Figure 2:
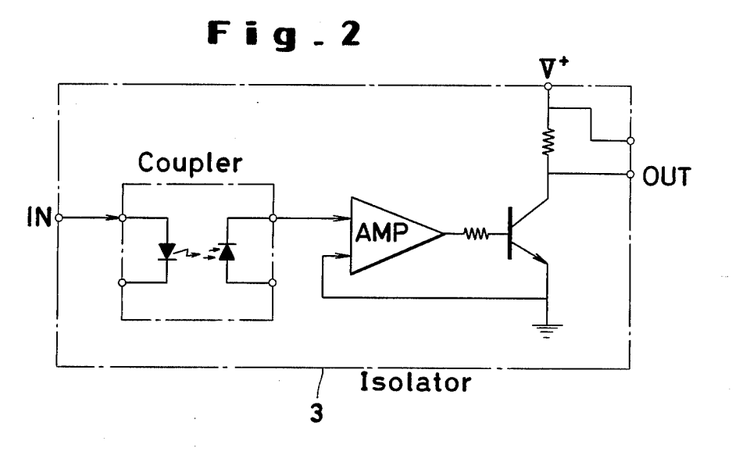
FIG. 2 is a detailed explanatory diagram of an isolator to be used in the apparatus for electrocutaneous stimuli of FIG. 1.

The information subjected to transmission to the subject is fed to the central processing unit 1 by via an input device such as a typewriter or image pickup tube (not shown), for example. The CPU processes this information, determines pulse height, pulse width and amplitude in accordance with the information and forwards the data on these factors to the stimulator 2. The stimulator 2 generates pulse signals in accordance with the data from the CPU and forwards the signals to the isolator 3. As the stimulator 2, any of the known devices may be used. For example, the device which has been suggested by the inventors in U.S. patent application Ser. No. 781,887 can be employed. The isolator 3 is required to be a device such that it will serve the purpose of substantially isolating analogue signals from the stimulator 2 and, at the same time, permit generation of certain degree of energy. Constant-current isolators and constant-voltage isolators fulfill the requirement. The block diagram of a typical constant-current isolator is illustrated in FIG. 2. In this isolator is used an analogue photocoupler which possesses a function of amplifying electric current. It additionally incorporates various compensation circuits and driving circuits effective such as for controlling electric current and checking reverse current, though these are not shown in the diagram.

The pulse signals which have been transferred to the isolator 3 of the construction described above are first subjected to isolation effected by the analogue photocoupler and then forwarded to the current-amplifying circuits and to the analogue switches 9 which are connected to the outputs of the circuits. These analogue switches are set or reset by the signals which result from the isolation of the output of the decoder 7 by the digital photocoupler 8. Consequently, the signals with amplified current which issue from the isolators are forwarded through the output terminals of those of the analogue switches designated by the decoder to the corresponding stimulation electrodes 5 held in contact with or inserted in the skin 6 of the subject. The term "reference electrode" as used herein means one of the pair of electrodes attached to the organism for delivery of electrocutaneous stimuli, which electrode is held on the side where no stimulus is felt by the organism. Ordinarily, this electrode is connected to the plus terminal of the isolator.

An experiment conducted by the inventors has shown that within a specific frequency range, different pulse signals applied to an electrode produce one and the same magnitude of sensation on the human subject insofar as the products of pulse widths multiplied by the squares of respective pulse heights are equal. This indicates that the parameters available independently for conversion of information into pulse signals are limited to the frequency of pulses involved and the pulse energy. With these parameters alone, therefore, the volume of information which can be transmitted is limited. Where the information to be transmitted is complicated or where numerous items of information are to be simultaneously transmitted to the subject, desired transmission of information may possibly be accomplished by use of an apparatus having a multiplicity of stimulators $2_1, 2_2, \ldots 2_{15}, 2_{16}$ connected to one side to the CPU 1 and on the other side to as many pairs of electrodes 4, 5 attached to the skin through the medium of expensive isolators 3 serving to guarantee the independence and safety of the individual electrodes, whereby the transmission is effected by relevant stimulators 2 issuing pulse signals in response to the command signal from the CPU 1 and presenting these pulse signals through the corresponding isolators to those pairs of electrodes to which said stimulators are connected.

Figure 3:
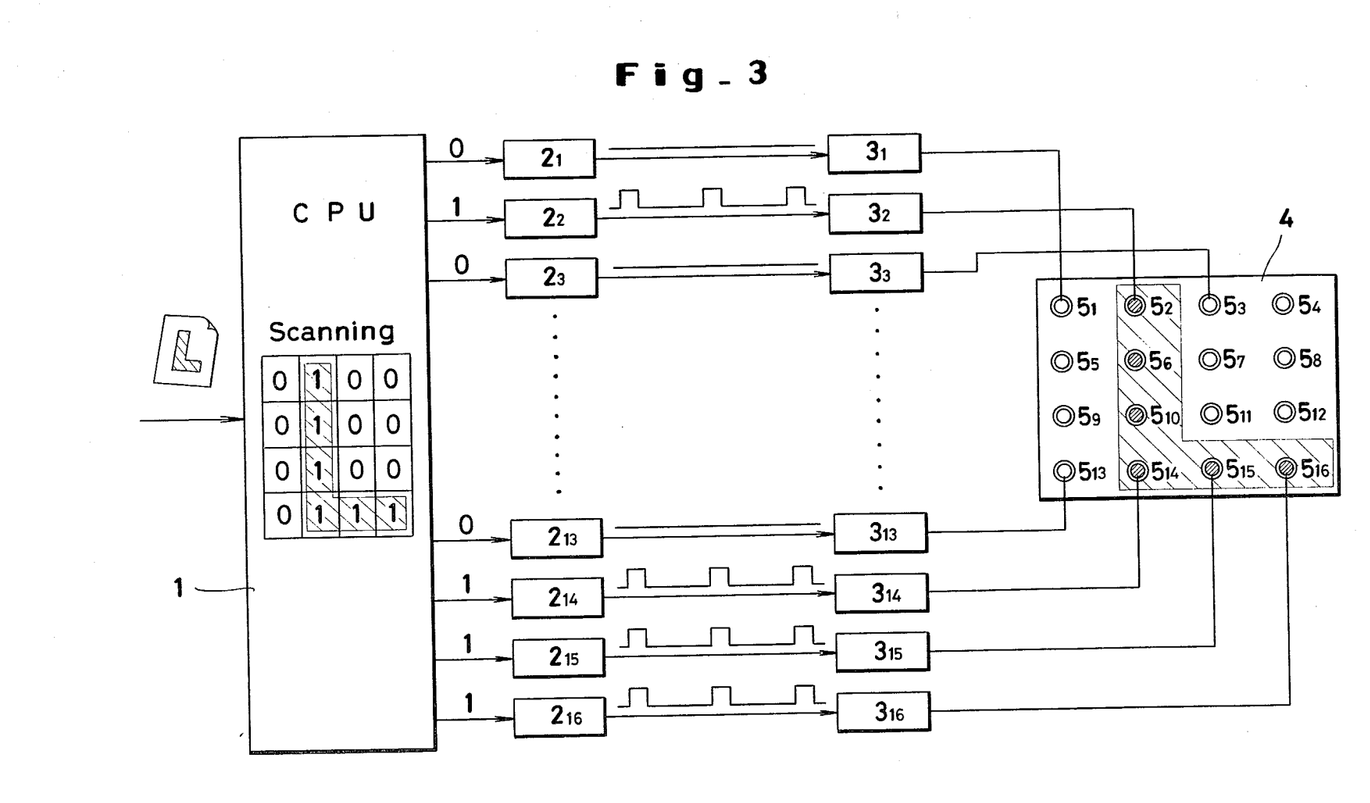
FIG. 3 is an explanatory diagram illustrating an apparatus using a plurality of stimulators of the construction in the apparatus of FIG. 1, so as to permit pulse signals issuing from the plurality of stimulators to be applied simultaneously to the plurality of electrodes.

The operation of this apparatus will be described by citing a case wherein 16 electrodes are disposed at suitable parts on the subject's back, arms, etc. and one item of information, the letter "L", for instance, is transmitted by means of these electrodes. In this case, the apparatus requires 16 stimulators and as many isolators as a matter of course, though one reference electrode is shared by all the isolators in use. As the letter "L" is introduced through the input device 7 into the CPU 1, the CPU 1 issues signals to the stimulators $2_2$, $2_6$, $2_{10}$, $2_{14}$, $2_{15}$ and $2_{16}$. In these stimulators, the signals are processed in the same way as previously described with reference to the apparatus of FIG. 1, to generate pulse signals conforming with the command from the CPU 1. These pulse signals are forwarded through relevant isolators to the respective electrodes. The pulse signals which are thus transmitted to the electrodes may be diagrammatically represented as shown in FIG. 3. As the result, the subject perceives the information, namely the letter "L", by the stimuli applied to the skin.

Unfortunately, the apparatus incorporating so many stimulators and isolators as described above is voluminous and economically disadvantageous. What is more, it is highly dangerous to deliver a lot of electric energy all at once to the human body.

Figures 4, 5:
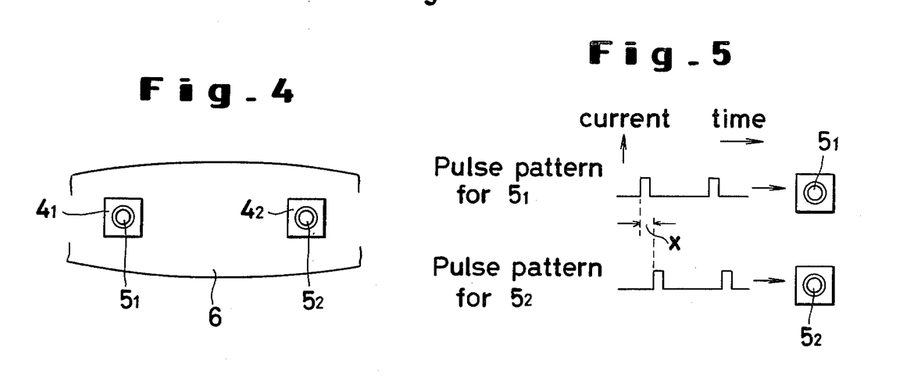
FIG. 4 is an explanatory diagram showing two electrodes attached to the human body.
FIG. 5 is an explanatory diagram illustrating the time lag involved in the application of pulse currents to the two electrodes of FIG. 4.

The inventors' experiments have demonstrated that when pulse signals are applied to the two pairs of electrodes $4_1$, $5_1$ and $4_2$, $5_2$ disposed at a prescribed interval from each other on the skin as illustrated in FIG. 4 so as to give stimuli to the skin, the subject feels as if the two stimuli are applied to the respective electrodes at substantially the same moment insofar as the time delay between the two pulse signals does not exceed 15 ms but that, when the time delay exceeds the limit of 15 ms, he feels the stimuli occur at different moments.

When pulse signals of one same pattern are applied to both the electrodes $5_1$, $5_2$ with a timing shown in FIG. 5, the respective electric stimuli are simultaneously sensed in the electrodes insofar as the delay "x" in the time of their application does not exceed 15 ms. In other words, such electric stimuli are sensed at the same frequency as that of the pulse signals involved. As the delay in the time of application increases beyond the limit of 15 ms, the electric stimuli are sensed separately.

Figure 6:
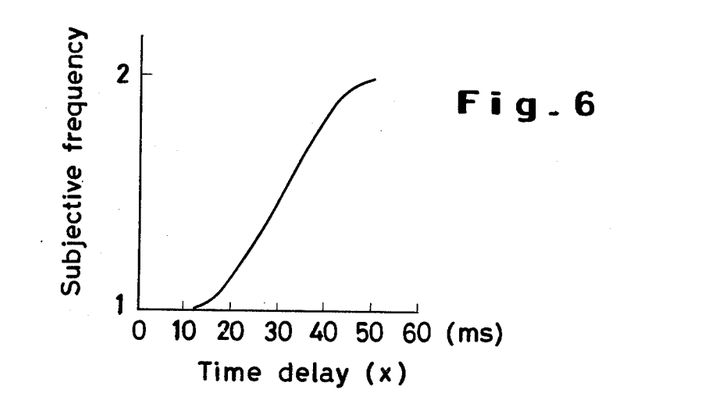
FIG. 6 is a graph showing the relation between the time lag involved in the application of pulse currents to the two electrodes and the subjective frequency sensation caused in the human body.

The relation between the time delay in the application of two pulse signals involving a pulse interval of 100 ms and the subjective frequency of electric stimuli perceived by the human subject was investigated. The results were as shown in FIG. 6. In the graph of FIG. 6, the horizontal axis represents the time delay in the application of said two pulse signals and the vertical axis the subjective frequency. It is found from this graph that electric stimuli are simultaneously sensed in the electrodes at the same frequency as that of one pulse signal when the time delay does not exceed 15 ms, and that the sensation of the frequency of electric stimuli increases to two times when the time delay increases to 50 ms. In other words, the subject never has the impression that two pulses separated by 20 ms or more are simultaneous.

If instead of an apparatus capable of effecting the transmission of complicated information or a multiplicity of items of information by simultaneously applying pulse signals to a multiplicity of electrodes as illustrated in FIG. 3, there is adopted an apparatus capable of causing a plurality of pulse signals to be sequentially applied to the respective electrodes with a time delay not exceeding 15 ms, there can be generated the same electric stimuli. This apparatus, therefore, functions effectively with one stimulator and one isolator. Since the electric stimuli are generated sequentially in the subject's organism, the magnitude of electric stimuli applied at any given moment is small enough to obviate the otherwise possible danger of electric shock.

The present invention has issued from the discovery described above. Now, it will be specifically described with reference to FIG. 7.

Figure 7:
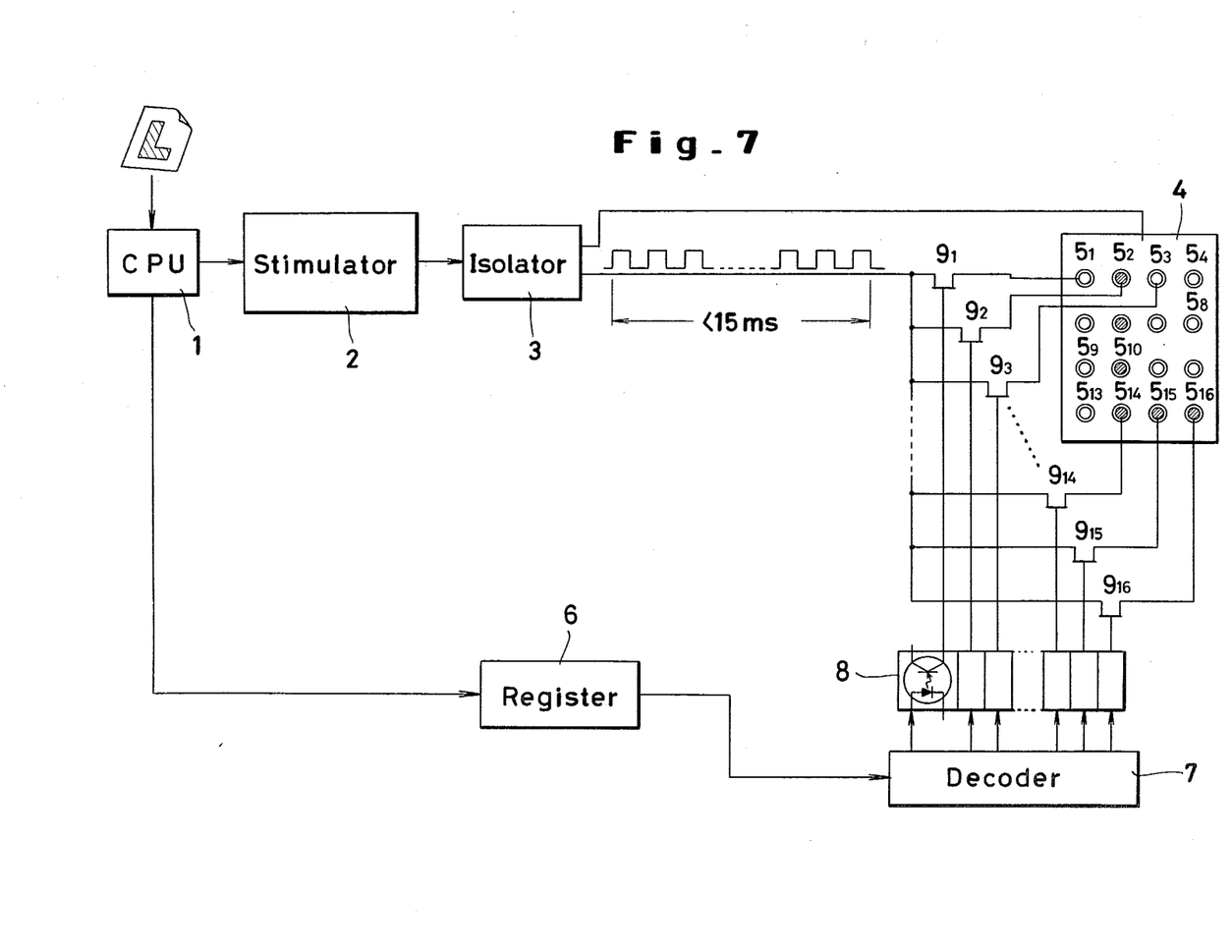
FIG. 7 is a block diagram illustrating one embodiment of the apparatus of this invention for the transmission of information by the medium of electrocutaneous stimuli.

With reference to FIG. 7, the information to be conveyed is fed by the input device (not shown) to the CPU 1. The CPU 1 processes the received information, determines pulse height, pulse width and amplitude in accordance with the information and forwards the data thus determined to the stimulator 2. The stimulator generates a train of pulse signals possessed of a parameter designated by the command from the CPU 1 and issues them through the isolator 3 to the multiplicity of electrodes $5_1$, $5_2$, ... $5_{15}$ and $5_{16}$. An analogue isolator possessed of a low-voltage power source and illustrated in FIG. 2 is used as the isolator 3. The multiplicity of electrodes are provided at their respective input sides with analogue switches $9_1$, $9_2$ ... $9_{15}$ and $9_{16}$. The "ON-OFF" operation of these analogue switches is performed by the decoder 7 to which the analogue switches are connected via the isolators 8. As the stimulator, the isolator, the analogue switches, the decoder and the register, there may be used any of the known devices.

In the apparatus of the construction described above, when the information to be conveyed is fed by the input device into the CPU 1, the data resulting from the processing of the information in the CPU 1 are delivered to the stimulator 2. At the same time, the CPU 1 transmits to the register 6 a code signal for the operation of analogue switches 8. The series of pulse signals generated by the stimulator 2 in accordance with the command from the CPU 1 are forwarded through the isolator 3 to the analogue switches of the electrodes. At this point, the decoder 7 transmits the electric signal to only those of the analogue switches which are to be set to the "ON" state in accordance with the command from the register 6. This electric signal is intended exclusively for effecting the selection of the "ON-OFF" state of the analogue switches. It is electrically isolated by the mono-element isolator 8 such as of a photocoupler from devices for application of stimuli and forwarded to the analogue switch gate of the relevant electrode.

Figure 8:
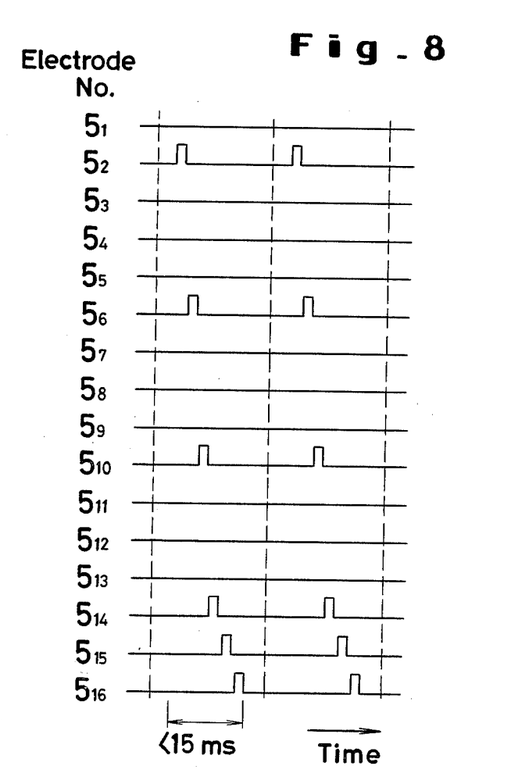
FIG. 8 is an explanatory diagram showing the relation between the pulse signals applied to the individual electrodes of the apparatus of FIG. 7 and the time delay.

The pulse signals generated in one train from the stimulator as described above are sequentially forwarded to the analogue switches of all the electrodes. Since the "ON-OFF" control of the analogue switches is effected by the command signal from the decoder, only the selected ones of the analogue switches are caused to assume the "ON" state successively and no two analogue switches are allowed to assume the "ON" state simultaneously. Therefore, the electric stimuli are imparted at certain time intervals as illustrated in FIG. 8. As described previously, however, when all the pulse signals of one train are applied within 15 ms, the human subject cannot perceive the presence of such time intervals. When the "ON-OFF" operation of the analogue switches is carried out on the order of a few tens of μs and pulse signals having a fixed width of 100 μs are successively applied to 150 electrodes, the human subject cutaneously perceives that the electric stimuli have been received practically at the same moment.

Now the application of the apparatus of the present invention to the conveyance of the letter "L" to the subject will be described.

When the letter "L" as the information is fed to the CPU 1 by the input device, the CPU 1 gives to the stimulator a command to issue six pulse signals possessed of fixed width and height and separated by fixed spaces. The stimulator generates the pulse signals in accordance with the command from the CPU 1 and forwards them successively to the array of electrodes. At the same time that the CPU 1 gives the command to the stimulator, the CPU 1 transmits through the register 6 to the decoder 7 a signal for causing the analogue switch $9_2$ to assume the "ON" state when the first of the series of six pulse signals is issued from the stimulator. Consequently, the first of the six pulse signals is applied to the electrode $5_2$. Similarly, the CPU 1 issues to the decoder 7 a signal for causing the analogue switch $9_6$ of the electrode $5_6$ to assume the "ON" state upon issuance of the second of the six pulse signals and then a signal for causing the analogue switch $9_{10}$ of the electrode $5_{10}$ to assume the "ON" state upon issuance of the third of the six pulse signals. By similarly causing the analogue switches of the electrodes $5_{14}$, $5_{15}$ and $5_{16}$ to assume the "ON" state upon successive issuance of the last three of the pulse signals from the stimulator 2 (FIG. 8), stimulating pulses are applied to the relevant electrodes. When the application of the series of pulse signals is completed within 15 ms, the subject can perceive the letter "L" on the skin.

As is evident from the foregoing description, when given information is conveyed by applying a plurality of electric stimuli to the skin, the subject perceives that the electric stimuli have been received at the same moment if the application of electric stimuli is completed in not more than 15 ms. Accordingly, the number of electrodes to which electric stimuli have been imparted for the transmission of information can be calculated on the basis of the length of time spent in the operation of analog switches, the width of pulse signals to be applied and the frequency of the stimuli. Let "t" ms stand for the time required for operating a single analog switch and imparting electric stimuli to the subsequent electrode, "W" ms for the width of pulse signal to be applied and "T" ms for the frequency, and the number of electrodes "N" which can be fastened to the skin can be calculated by the following formula in the case of the apparatus of FIG. 7.

$N < T/(W+t)$ where $T \leq 15$ $N < 15/(W+t)$ where $T > 15$

Figure 9:
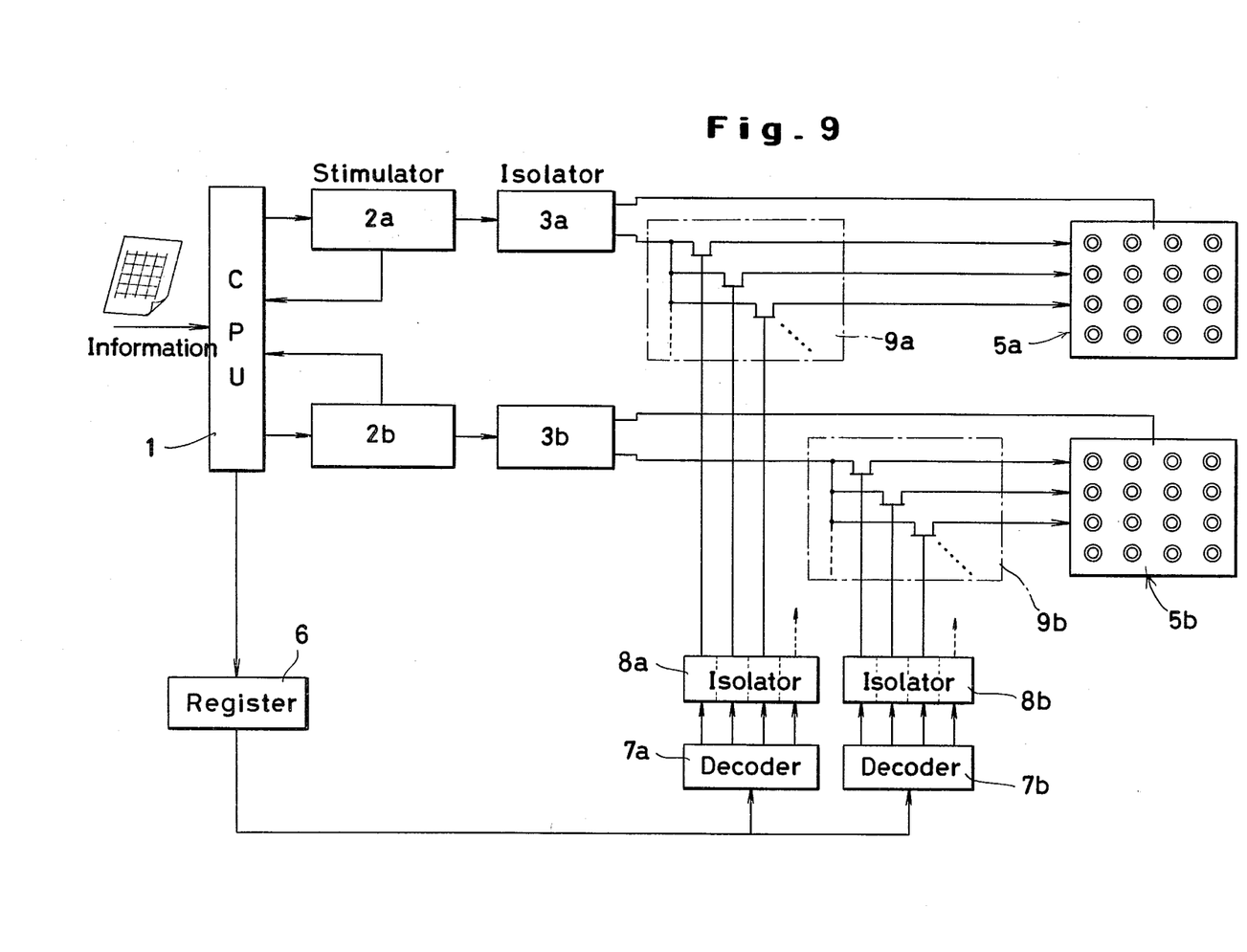
FIG. 9 is a block diagram illustrating another embodiment of the apparatus of this invention for the transmission of information by the medium of electrocutaneous stimuli.

Assume, for example, "t" to be $5 \times 10^{-3}$ ms, "W" to be $100 \times 10^{-3}$ ms and "T" to be 100 ms respectively, and there will be obtained $N < 15/(5+100) \times 10^{-3} \approx 142.8$, indicating that there can be installed a total of 142 electrodes.

Where there arises the necessity for installing a great many electrodes, it suffices to arrange two stimulators 2a, 2b, two isolators 3a, 3b, two decoders 7a, 7b and two groups of isolators 8a, 8b and connect two groups 5a, 5b of electrodes one each to the said isolators 3a, 3b as shown in FIG. 9. In this setup, the control of the "ON-OFF" operation of these groups of electrodes will be effected by means of the two decoders 7a, 7b. With this apparatus, there is a possibility that two pulse signals from the two stimulators 2a, 2b will be simultaneously applied to the subject. Since the magnitude of electric stimuli received is that from only two electrodes or so, however, there is no danger of electric shock.

The pulse signals to be sequentially applied to the individual electrodes are not always required to be identical with one another. After one pulse signal has been forwarded to one electrode, a pulse signal different from said pulse signal can be given to the next electrode by suitably revising the data stored in the stimulator between the time the first pulse signal is delivered to the first electrode and the time the operation of the analog switch of the next electrode is effected. Thus, the apparatus of this invention permits information of far more complicated nature to be transmitted effectively.

Of course, the electrocutaneous stimuli are sensed with time delay when the time delay involved in the application of pulse signals to the individual electrodes increases beyond 15 ms.

In the presentation of electrocutaneous stimuli to the human subject according to the information-transmitting apparatus of the present invention, electric pulses passed through a single isolator can be conveyed to prescribed electrodes sequentially yet substantially at the same moment without affecting the independency of said electrodes by controlling the relevant analog switches so as to provide their respective "ON-OFF" operations sequentially with a time delay brief enough for the resultant electric stimuli to cause virtually simultaneous cutaneous sensation on the part of the subject. Compared with the apparatus of a construction such as is illustrated in FIG. 3 which necessitates use of as many isolators as electrodes, the device of this invention effectively functions with only one isolator and, therefore, enjoys great economy in both size and cost of equipment.

When electric stimuli are applied exactly at the same moment through a multiplicity of electrodes to the human subject, the result is that a large magnitude of electric energy is instantaneously introduced into the subject's organism. This is a very dangerous situation. According to the information-transmitting apparatus of the present invention, although electric pulses are substantially simultaneously conveyed to the multiplicity of electrodes, it is to a very few electrodes that the pulses are delivered at practically the same moment. Thus, the apparatus of this invention guarantees complete safety of the subject from the electric stimuli to be involved, provides multi-point electric stimuli of widely varying patterns and permits transmission of a greater volume of information without entailing such a dangerous situation as mentioned above.

What is claimed is:

1. An apparatus for the transmission of information to a human subject by the medium of electric stimuli selectively presented to the subject's skin by the application of closely spaced-apart signals to electrodes attached to the subject's skin, which comprises:
   a central processing unit (CPU);
   a stimulator coupled to the central processing unit for issuing pulse signals having the parameters of the information to be transmitted;
   a plurality of electrodes for generating electrocutaneous stimuli to the subject in response to said pulse signals, wherein each of said electrodes includes an input for receiving the pulse signals;
   an analog switch connected to each of said electrode inputs;
   a first single isolator having its input connected to said stimulator and its output connected to the input of each analog switch of said electrodes.
   a decoder having its input coupled to the CPU for sequentially controlling the "ON-OFF" operation of the respective analog switches; and second isolators connecting said analog switches with said decoder so that the electric stimuli are selectively turned on and off by the CPU coupled to the decoder in pulsed intervals, whereby said analog switches are turned selectively.

2. The apparatus set forth in claim 1, wherein said first single isolator is an analog isolator having a low-voltage power source.

3. The apparatus set forth in claim 1, wherein said second isolators are photocouplers.

4. The apparatus set forth in claim 1, wherein the analog switches are sequentially controlled in less than 15 ms.

* * * * *